("12") United States Patent
Tsai et al.

(10) Patent No.: US 10,018,573 B2
(45) Date of Patent: Jul. 10, 2018

(54) DUAL-FUNCTION WAFER HANDLING APPARATUS (71) Applicant: TAIWAN SEMICONDUCTOR MANUFACTURING CO., LTD., Hsinchu (TW)

(72) Inventors: Ming-Han Tsai, Taichung (TW); Sheng-Hsiang Chuang, Hsinchu (TW); Guan-Cyun Li, Toufen Town (TW); Yen-Ju Wei, Taichung (TW); Chiung-Min Lin, Zhubei (TW); Yi-Ming Chen, New Taipei (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 63 days.

(21) Appl. No.: 14/513,072

(22) Filed: Oct. 13, 2014

(65) Prior Publication Data
US 2016/0103080 A1 Apr. 14, 2016

(51) Int. Cl.
*G01N 21/95* (2006.01)

(52) U.S. Cl.
CPC .............................. *G01N 21/9503* (2013.01)

(58) Field of Classification Search
CPC ........... G01N 21/9501; G01N 21/9505; G01N 21/9503
USPC .......................................... 356/237.4–237.5
See application file for complete search history.

(56) References Cited

U.S. PATENT DOCUMENTS 7,012,684 B1 * 3/2006 Hunter ............... G01N 21/8903
250/559.44
2007/0002316 A1 * 1/2007 Choi .................. G01N 21/9501
356/237.2

FOREIGN PATENT DOCUMENTS

KR 20020083282 A * 11/2002

OTHER PUBLICATIONS

Pending U.S. Appl. No. 14/276,545, filed May 13, 2014.

* cited by examiner

*Primary Examiner* — Hina F Ayub
*Assistant Examiner* — Amanda Merlino
(74) *Attorney, Agent, or Firm* — Maschoff Brennan (57) ABSTRACT

A dual-function wafer handling apparatus for handling a wafer includes an aligner for rotating the wafer, an ID reader disposed corresponding to an edge of the wafer for reading an ID of the wafer, and an optical defect inspection unit for capturing images to analysis.

20 Claims, 7 Drawing Sheets

DUAL-FUNCTION WAFER HANDLING APPARATUS

BACKGROUND

A conventional semiconductor fabrication plant typically includes multiple fabrication areas or stations interconnected by a bay. Each station generally includes the requisite fabrication tools to provide a particular semiconductor manufacturing process, such as photolithography, chemical-mechanical polishing, chemical vapor deposition, etc.

In the semiconductor manufacturing processes described above, defect inspection is carried out in some manufacturing processes. In the defect inspection, the surface of the semiconductor wafer is inspected to see if there are scratches, dust, cracks, stains or uneven portions manually. Defects such as cracks may result in the breaking of the wafer itself. Therefore, the presence or absence of defects at the wafer edge portion has to be detected as early a step as possible to determine whether the wafer is good or bad.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Conventionally, the wafer is manually inspected by an operator at an automated optical inspection (AOI) station, or set run-card for vis-edge tool offline check with a long time. Conventional wafer defect inspection not only spends lots of time, but also requires extra stations and operators. Furthermore, the conventional manual inspection only selects several wafers as samples among a wafer lot. The sampling rate of the conventional manual inspection is, for example, about 5%. Namely, only 5% of wafers have been edge-defect inspected during the semiconductor manufacturing processes.

In order to detect the defects at the wafer edge portion more efficiently, the present disclosure integrates a wafer defect detector with an inline apparatus for automatically detecting defects at the edge of the wafer at the same time of that the wafer is processed. Therefore, wafers need not be moved to an additional manual inspection station thereby reducing manual operations, and the sampling rate of the wafers is highly increased.

The inline apparatus is a regular apparatus, which processes almost every wafer. For example, in the manufacturing of a semiconductor device, the wafer or device is usually processed at many work stations or processing machines. The transporting or conveying system, such as an automatic material handling system (AMHS) has been used extensively in the semiconductor fabrication field. Therefore, the inline apparatus with wafer defect inspection function can be one of stations of the automatic material handling system.

The automatic material handling system includes a plurality of bays (rows) of storage areas. Each bay has a stocker, which includes bins for holding a plurality of containers or front opening unified pods (FOUPs). The stocker holds the containers or FOUPs in preparation for transporting a container or FOUP to the loadport of a processing tool. The automatic material handling system can divide wafers into lots that undergo different processing sequences.

Figure 1:
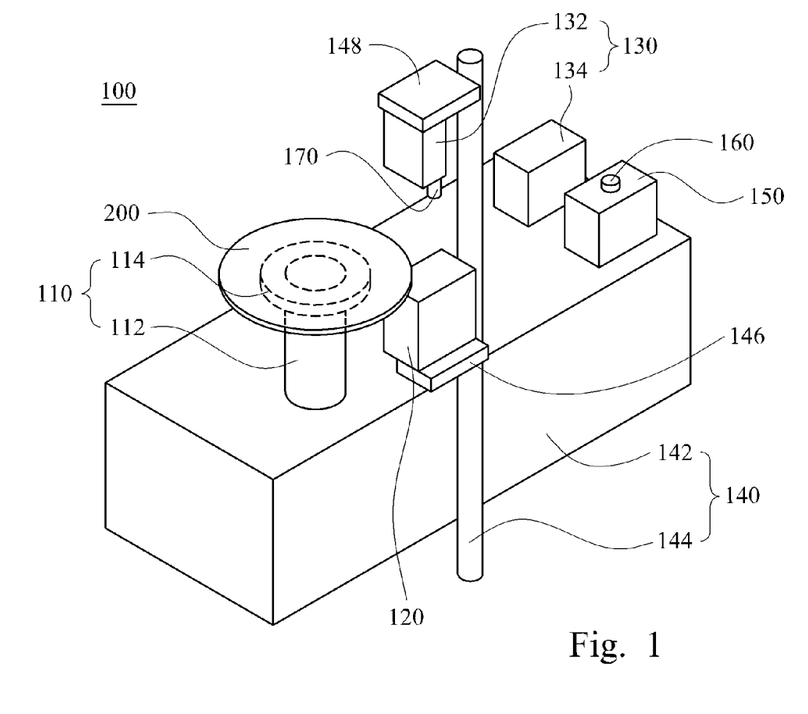
FIG. 1 is a schematic diagram of a dual-function wafer handling apparatus, in accordance with some embodiments.

FIG. 1 is a schematic diagram of a dual-function wafer handling apparatus, in accordance with some embodiments. The dual-function wafer handling apparatus 100 is one of the stations in the automatic material handling system. The dual-function wafer handling apparatus 100 includes an aligner 110, an ID-reader 120, an optical defect inspection unit 130, a frame 140 for fastening the aligner 110, the ID-reader 120 and the optical defect inspection unit 130, and a control unit 150 for controlling the aligner 110 and the ID reader 120. The dual-function wafer handling apparatus 100 is arranged near a stocker for sorting and inspecting wafers 200.

The wafers 200 fabricated in the semiconductor fabrication process each has their own IDs, which are located opposite a notch or an orientation flat at the wafers 200. The IDs are data matrix codes which contain a lot number and a barcode, and are formed on the wafers 200 by a laser. The IDs of each wafer 200 are different from each other to allow easy recognition of the wafers 200. The dual-function wafer handling apparatus 100 with the aligner 110 and the ID reader 120 can recognize automatically the ID of the wafer 200. The aligner 110 includes a motor 112, and a rotatable disk 114 driven by the motor 112. The wafer 200 is transferred and placed on the rotatable disk 114. For example, the wafer 200 is transferred from a FOUP to the aligner 110 by a robot arm. When the control unit 150 detects that the wafer 200 is positioned on the rotatable disk 114, the control unit 150 sends a command to trigger the aligner 110. The aligner 110 rotates the wafer 200 at a constant rotating speed and detects the center position of the wafer 200 and the direction in which the notch or the orientation flat is present. Therefore, the wafer 200 is aligned on the aligner 110. The image of the ID of the wafer 200, which is formed opposite to the notch or the orientation of the wafer 200, is captured and identified by the ID reader 120, then the ID information of the wafer 200 is sent to the control unit 150 for later sorting.

Also, after the wafer 200 is aligned on the aligner 110, the control unit 150 sends a command to initial the optical defect inspection unit 130. The optical defect inspection unit 130 includes an image sensor 132 and an automatic optical inspection processor 134. The image sensor 132 is, for example, a charge-coupled device (CCD). The image sensor 132 is triggered by the optical inspection processor 134 to capture images of the edge of the wafer 200 while the wafer 200 is rotated by the rotatable disk 114. The images captured by the image sensor 132 are sent to the optical inspection processor 134 for analysis. The rotating speed of the rotatable disk 134 can be controlled according the image capturing frequency of the image sensor 132. If the analysis result of the images of the edge of the wafer 200 is normal, that means the wafer 200 passes the inspection, and the wafer 200 is conveyed to the next process from the aligner 110. However, if the analysis result of the images of the edge of the wafer 200 is abnormal, that means the wafer 200 has defects and cannot pass the inspection, and the dual-function wafer handling apparatus 100 sends an alarm to tell operator the failed wafer 200 needs to be removed.

The frame 140 includes a platform 142, a rod 144 standing next to the platform 142, and a first holder 146 and a second holder 148 fastened on the rod 144. The second holder 148 is arranged higher than the first holder 146. The aligner 110 is placed on the platform 142. The ID reader 120 is placed on the first holder 146, and the image sensor 132 is placed on the second holder 148. In some embodiments, the image sensor 132 is fastened at a side or a bottom of the second holder 148. The ID reader 120 and the image sensor 132 are located corresponding to the edge of the wafer 200 for capturing images of the edge of the wafer 200. In some embodiments, the ID reader 120 and the image sensor 132 are arranged at opposite sides of the wafer 200. For example, the ID reader 120 is disposed under the wafer 200, and the image sensor 132 is disposed above the wafer 200. Namely, the wafer 200 is disposed between the ID reader 120 and the image sensor 132. The ID reader 120 reads the ID from the bottom of the wafer 200 after the notch or orientation flat is found on the wafer 200. The image sensor 132 captures images of the edge of the wafer 200 when the wafer 200 is rotated by the aligner 110.

The dual-function wafer handling apparatus 100 provides functions of automated sorting and automated defect inspection. The dual-function wafer handling apparatus 100 is one of the stations in the automatic material handling system, which is widely used in the semiconductor fabrication plant. Therefore, each wafer 200 of the wafer lots can be inspected automatically while being sorted. The sampling rate of the wafers 200 becomes 100%, and no extra outline inspection station is needed.

By using the dual-function wafer handling apparatus 100 discussed above, during the observation of the edge of the wafer 200, adjustment can be made to the wafer 200 position so that the edge of the wafer 200 can be located at the position under the image sensor 132, and adjustment can be made to the rotating speed to adjust the observation speed. For example, in some embodiments, the time for one-round wafer rotation is about 1 second; the image capturing frequency of the image sensor 132 is about 65 frames per second; and the view of field is about 43*32 mm². The image sensor 132 captures the images continuously while the wafer 200 is rotated by the aligner 110. Because the ID reader 120 identifies the wafer 200 at the same time while the image sensor 130 captures the images, the wafer 200 rotates at least one round on the aligner 110. Therefore, the image sensor 132 can capture images of complete circumference of the wafer 200. The plurality of images have overlapping regions of the wafer 200.

Figure 2:
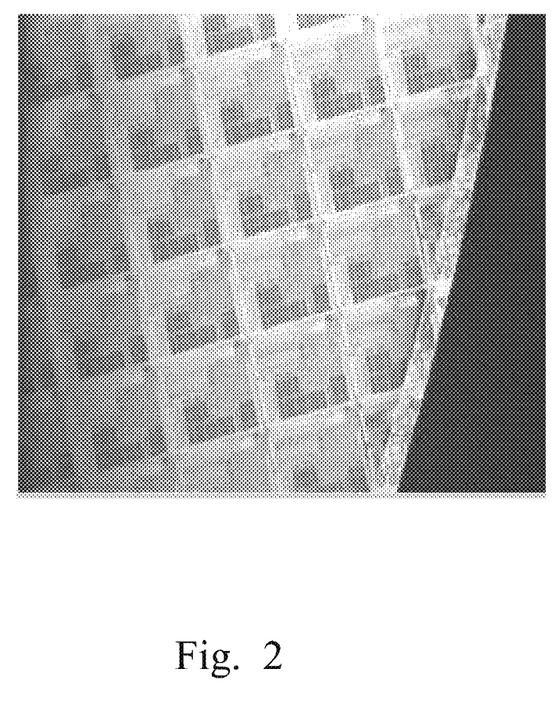
FIG. 2 and FIG. 3 are image and analysis result of an example of a normal wafer.
Figure 3:
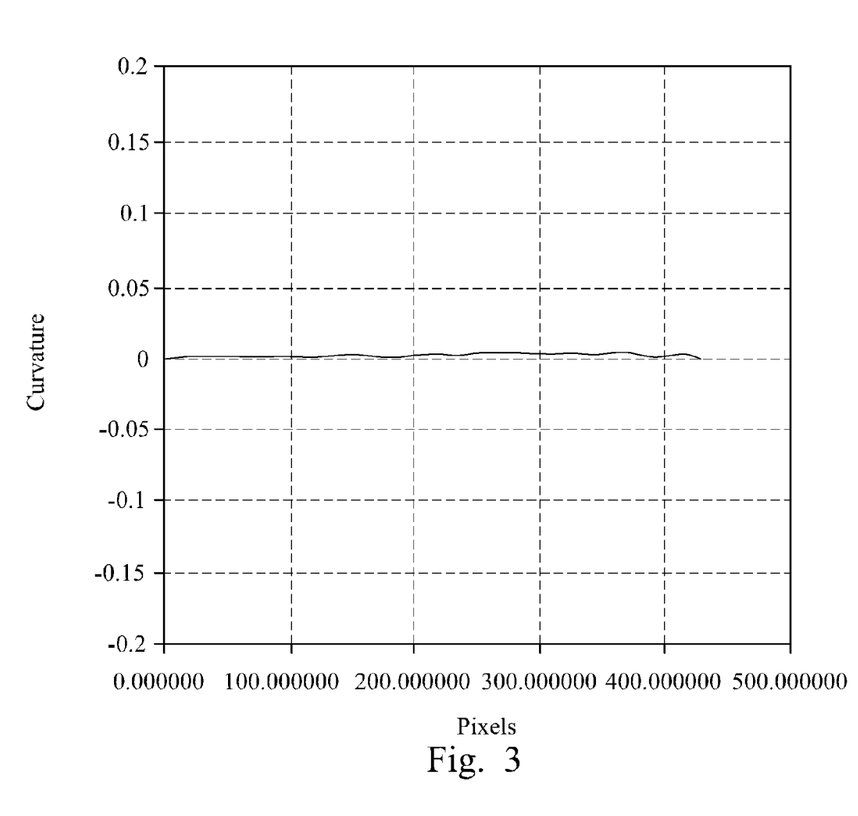

FIG. 2 and FIG. 3 are image and analysis result of an example of a normal wafer. The images of the edge of the wafer are captured by the image sensor and are sent to the optical inspection processor for analysis. The optical inspection processor captures the profile of the wafer and calculates the curvature of the wafer at each frame. The data of the curvatures of frames are collected, such that the analysis result shown in FIG. 3 is provided. The normal wafer has a smooth and continuous curved profile. Namely, the curvature of the profile of the normal wafer (excluding the notch portion) can be regarded as constant in FIG. 3.

Figure 4:
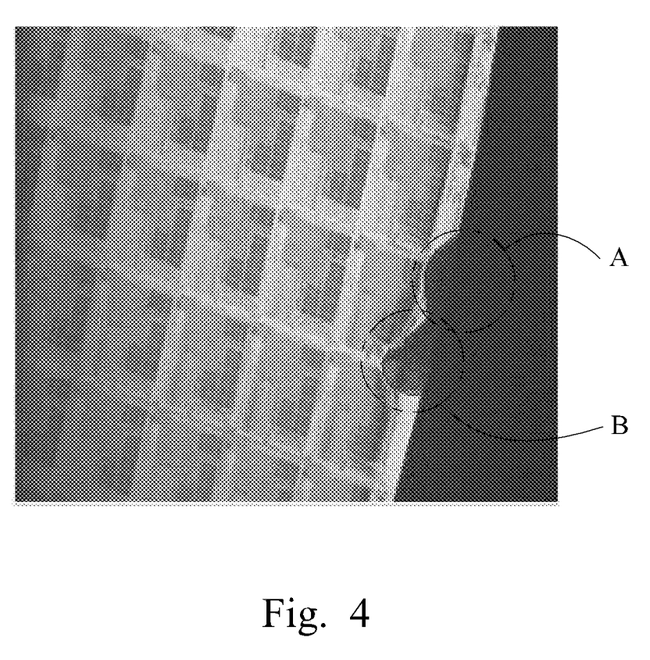
FIG. 4 and FIG. 5 are image and analysis result of an example of an abnormal wafer.
Figure 5:
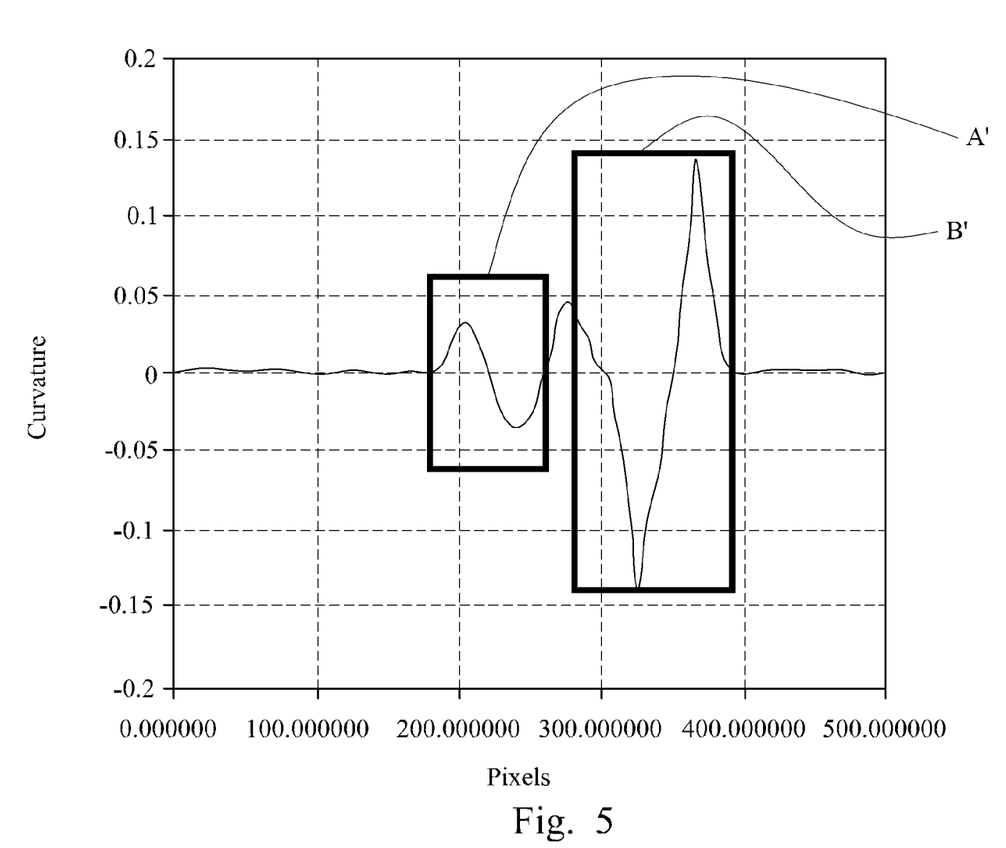

FIG. 4 and FIG. 5 are image and analysis result of an example of an abnormal wafer. The images of the edge of the wafer are captured by the image sensor and are sent to the optical inspection processor for analysis. However, the profile of the abnormal wafer is not smooth and continuous, thus the curvature of the abnormal wafer is not constant. For example, there are two concave areas and at the edge of the wafer, one is a notch A, and the other one is a chipping B. The notch A is arranged opposite to the ID of the wafer in order to identify the position of the ID more easily. The profile of the notch A is predetermined, thus the curvature A' of the notch A is predetermined and regular in FIG. 5. However, the defects, such as the chipping B, at the wafer have various types and various shapes, thus the profile of the abnormal wafer is broken. For example, the curvature B' of the abnormal wafer at the chipping B is irregular in FIG. 5.

As discussed from FIG. 2 to FIG. 5, the images of the complete circumference of the wafer are captured by the image sensor, and the profiles of the wafer in the images are calculated thereby obtaining the curvature of the wafer. The curvature of the wafer at the defect is irregular and can be distinguished from the curvature of the notch. When the optical inspection processor detects the irregular curvature, the wafer is determined abnormal and fails the inspection. Defects existing on the edge of the circumference of the wafer, such as wafer chipping, cracks, and a rinse cut amount, can be detected by this manner, and the abnormal wafer is early detected and is prevented from being made in the photolithography step executed after the application of photoresist.

Reference is made back to FIG. 1. In some embodiments, the dual-function wafer handling apparatus 100 is a sorter integrated with an automatic optical defect inspection unit. The sorter itself is an inline apparatus and is widely utilized in the semiconductor fabrication field. Almost each and every wafer 200 is processed by the sorter for being identified and conveyed to the predetermined station. By using the dual-function wafer handling apparatus 100, the process of inspection defects on the wafer 200 is made automatically while the wafer 200 is sorted. Therefore, the wafer 200 needs not be moved to an outline apparatus, and the sampling rate of wafer inspection is raised to about 100%. Namely, the wafer defect inspection is made inline the fabricating process, and the inspection result can report to the operator.

The dual-function wafer handling apparatus 100 further includes a warning device 160. The warning device 160 is electrically connected to the control unit 150. The analysis result of the optical inspection processor 134 is sent to the control unit 150. If the analysis result provided by the optical inspection processor 134 is normal, that means the wafer 200 on the aligner 110 passes the inspection, and the wafer 200 can go to next process according to the ID information provided by the ID reader 120. For example, the wafer 200 is moved from the aligner 110 to the FOUP. If the analysis result provided by the optical inspection processor 134 is abnormal, that means the wafer 200 does not pass the inspection, and the control unit 150 sends a signal to trigger the warning device 160 in order to tell the operator to remove the wafer 200 with defects.

The warning device 160 can be, for example, a sound alarm and/or an optical alarm. The quantity of the sound and/or the light generated by the warning device 160 is great enough to warn the operator that the wafer 200 processed by the dual-function wafer handling apparatus 100 is with defects. The wafer 200 with defects would stay on the aligner 110 until the operator shuts down the warning device 160 and removes the wafer 200 with defects.

The dual-function wafer handling apparatus 100 optionally includes a light source 170. The light source 170 is also disposed on the second holder 148. The light source 170 is disposed close to the image sensor 132 in order to provide lights to the wafer 200 for improving the quality of images captures by the image sensor 132. In some embodiments, the light source 170 is a co-axial light source providing co-axial lights with the image sensor 132 to the wafer 200. The positions of the image sensor 132 and the light source 170 can be adjusted via the frame 140. In some embodiments, the dual-function wafer handling apparatus 100 further includes an objective lens disposed in front of the image sensor 132. The image sensor 132 captures images through the use of the objective lens. When the edge portion of the wafer 200 is inspected, the edge portion of the wafer 200 is adjusted for being under the objective lens. After the wafer edge portion is adjusted to the position under the objective lens in this manner, the image sensor 132 begins to capture images. The images of the wafer edge portion obtained with the image sensor 132 are sent to the optical inspection processor 134 for analysis as discussed previously.

Figure 6:
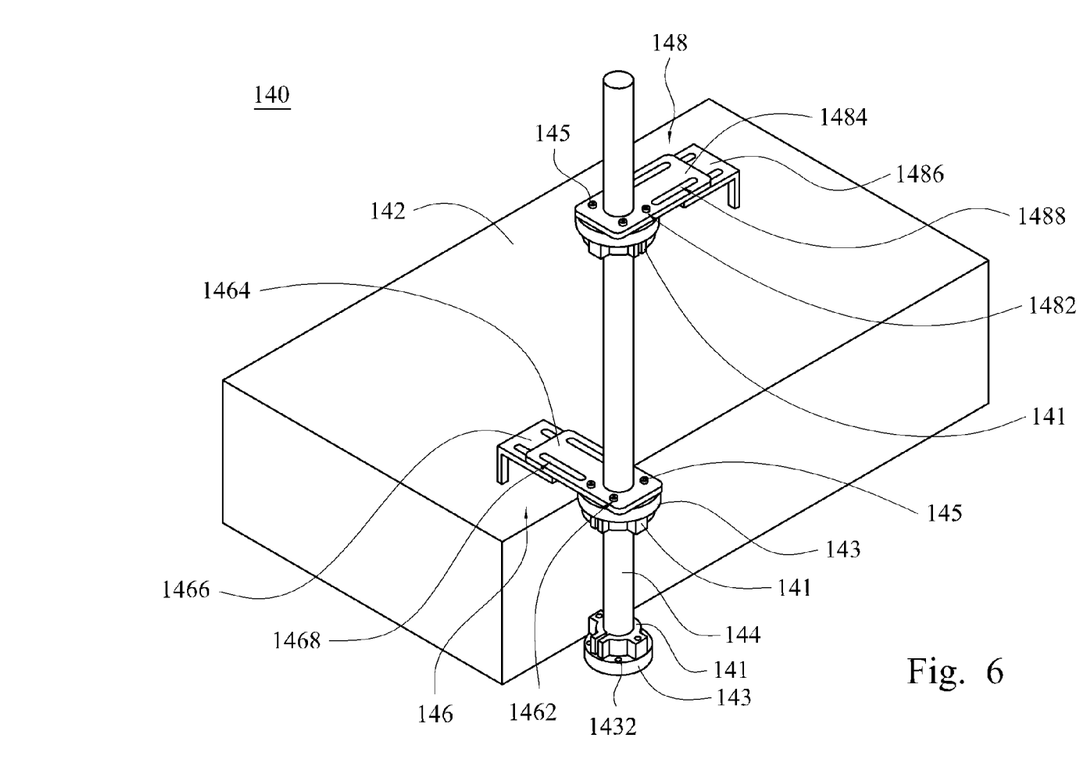
FIG. 6 is an oblique view of the frame of the dual-function wafer handling apparatus, according to some embodiments.

FIG. 6 is an oblique view of the frame of the dual-function wafer handling apparatus 100, according to some embodiments. The frame 140 includes the platform 142, the rod 144, the first holder 146, and the second holder 148. The platform 142 is utilized for placing the aligner thereon. The rod 144 is disposed next to the platform 142. The first holder 146 and the second holder 148 are fastened on the rod 144. The second holder 148 is arranged higher than the first holder 146. In some embodiments, the first holder 146 is utilized for placing the ID reader thereon, and the second holder 148 is utilized for placing the image sensor and the light source thereon. In some embodiments, the first holder 146 is utilized for placing the image sensor and the light source thereon, and the second holder 148 is utilized for placing the ID reader thereon. The heights of the first holder 146 and the second holder 148 can be adjusted, such that the first holder 146 and the second holder 148 are both disposed under the aligner, or the first holder 146 and the second holder 148 are both disposed above the aligner, or the first holder 146 and the second holder 148 are disposed at opposite sides of the aligner.

The position of the first holder 146 and the second holder 148 on the rod 144 can be adjusted. For instance, the rod 144 is a lead screw, and the first holder 146 and the second holder 148 are fastened on the rod 144 with the retaining nuts 141 and washers 143, in which the retaining nuts 141 are screwed or clamped on the rod 144 and the washers 143 are arranged between the retaining nuts 141 and the first holder 146 or the second holder 148. The first holder 146 and the second holder 148 are moved to the predetermined position and are supported by the retaining nuts 141. The position of the first holder 146 and the second holder 148 can be adjusted by releasing the retaining nuts 141, changing the position of the first holder 146 and the second holder 148, and re-fastening the retaining nuts 141.

The material of the rod 144, the first holder 146, the second holder 148, the retaining nuts 141 and the washers 143 is metal. In some embodiments, the rod 144 is made of steel, and the first holder 146, the second holder 148, the retaining nuts 141 and the washers 143 are made of aluminum alloy.

In some embodiments, the frame 140 further includes plural bolts 145 for fastening the first holder 146 and the second holder 148 to the washers 143. For example, the washer 143 has screw holes 1432 thereon, and the first holder 146 has plural through holes 1462 thereon. The bolts 145 pass through the through holes 1462 and screwed with the screw holes 1432, such that the first holder 146 is fastened on the washer 143. Similarly, the second holder 148 has plural through holes 1482 thereon, and the bolts 145 pass through the through holes 1482 and screwed with the screw holes 1432, such that the second holder 148 is fastened on the washer 143.

In some embodiments, the length of the first holder 146 and the second holder 148 can also be adjusted to fit the size of the image sensor and the ID reader. The first holder 146 includes a plate portion 1464 and a flange portion 1466. The plate portion 1464 has the through holes 1462 and is supported by the retraining nuts 141 and washer 143. The flange portion 1466 has flanges. Both the plate portion 1464 and the flange portions 1466 have slots 1468 thereon. The bolts and the nuts can be utilized for screwing the plate portion 1464 and the flange portion 1466. The screwing position in the slots 1468 can be changed to change the relative position between the plate portion 1464 and the flange portion 1466, such that the length of the first holder 146 can be adjusted. Similarly, the second holder 148 includes a plate portion 1484 and a flange portion 1486. The plate portion 1484 has the through holes 1482 and is supported by the retraining nuts 141 and washer 143. The flange portion 1486 has flanges, and the image sensor is fastened at the flange portion 1486. Both the plate portion 1484 and the flange portions 1486 have slots 1488 thereon. The bolts and the nuts can be utilized for screwing the plate portion 1484 and the flange portion 1486. The screwing position in the slots 1488 can be changed to change the relative position between the plate portion 1484 and the flange portion 1486, such that the length of the second holder 148 can be adjusted.

The frame 140 provides horizontal adjusting function to the first holder 146 and the second holder 148 via changing the position of the retaining nuts 141 fastened at the rod 144. The frame 140 also provides vertical adjusting function to the first holder 146 and the second holder 148 via changing the screwing position between the plate portions 1464, 1484 and the flange portion 1466, 1486. Since the horizontal position and the vertical position of the first holder 146 and the second holder 148 can be adjusted, the arrangement of the first holder 146 and the second holder 148 is more flexible. Thus the image sensor and the ID reader on the first holder 146 and the second holder 148 can be arranged corresponding to the edge of the wafer.

Figure 7:
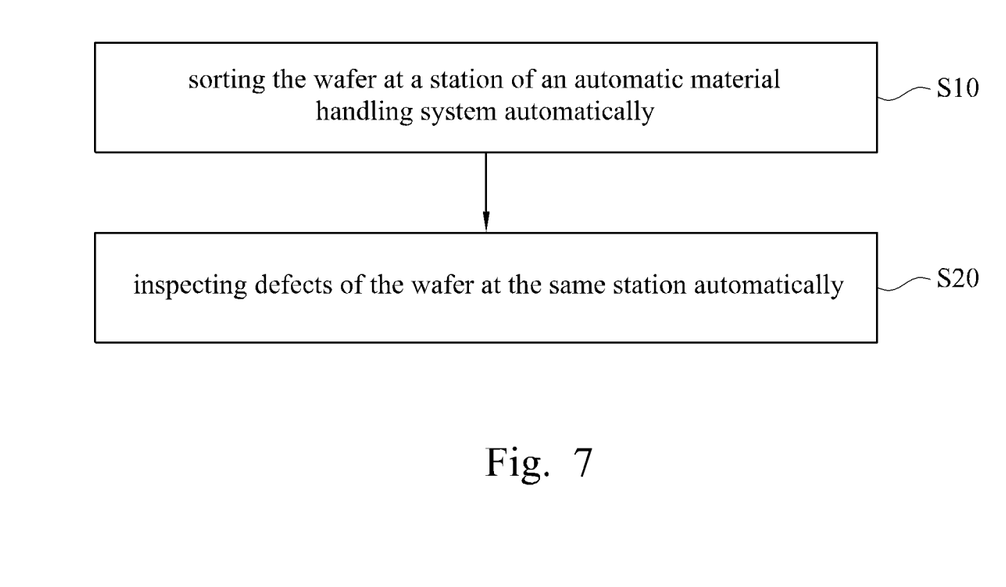
FIG. 7 is a flow chart of a method for handling a wafer, according to some embodiments.

FIG. 7 is a flow chart of a method for handling a wafer, according to some embodiments. The method uses an inline apparatus to handle the wafer. The method includes step S10 and step S20. In step S10, the wafer is sorted at a station of an automatic material handling system, for example, by an ID reader automatically. In step S20, the wafer is defect inspected at the same station by an image sensor automatically. Therefore, the station utilized in the method provides both functions of sorting and defect inspection. The steps S10 and S20 can be performed individually or simultaneously. In some embodiments, the wafer is inspected when sorting the wafer.

The present disclosure provides a dual-function wafer handling apparatus. The dual-function wafer handling apparatus is an apparatus with an aligner and provides the function of defect inspection. The defects of the wafer are inspected by capturing the profile of the wafer and analysis the curvature of the wafer. In some embodiments, the dual-function wafer handling apparatus provides both functions of sorting and defect inspection. The functions of sorting and the defect inspection are performed by the dual-function wafer handling apparatus automatically. Thus the sampling rate and accuracy of wafer defect inspection are highly improved. In some embodiments, the act of sorting is made when the defect inspection process is preformed. The dual-function wafer handling apparatus is an inline apparatus. Therefore, the wafer needs not be moved to an outline station for inspection. For example, the dual-function wafer handling apparatus can be a station of the automatic material handling system. The automatic material handling system is widely utilized in the semiconductor plant. Therefore, no extra station is required for wafer defect inspection. The frame for assembling the image sensor and the ID reader is adjustable. The position of the image sensor and the ID reader can be adjusted vertically and horizontally, such that the image sensor and the ID reader are positioned corresponding to the edge of the wafer.

According to some embodiments, an aspect of the disclosure provides a dual-function wafer handling apparatus for handling a wafer. The apparatus includes an aligner for rotating the wafer, an ID reader disposed corresponding to an edge of the wafer for reading an ID of the wafer, and an optical defect inspection unit for capturing images to analysis.

According to some embodiments, an aspect of the disclosure provides a dual-function wafer handling apparatus for handling a wafer. The apparatus includes an aligner for rotating the wafer, an ID reader for reading an ID of the wafer, an image sensor for capturing an image of an edge of the wafer, an optical inspection processor for capturing a profile of the edge of the wafer and calculating a curvature of the profile for analysis, and a frame for arranging the ID reader and the image sensor corresponding to the edge of the wafer.

According to some embodiments, an aspect of the disclosure provides method for handling a wafer. The method includes sorting the wafer at a station of an automatic material handling system automatically, and inspecting defects of the wafer at the same station automatically.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A dual-function wafer handling apparatus for handling a wafer, the apparatus comprising:
    a platform;
    an aligner disposed on the platform and configured to rotate the wafer;
    an ID reader configured to read an ID of the wafer;
    an optical defect inspection unit comprising an image sensor configured to capture images of the wafer for analysis;
    a rod;
    a first holder connected to the rod and holding the ID reader; and
    a second holder fastened on the rod and holding the optical defect inspection unit.

2. The dual-function wafer handling apparatus of claim 1, wherein the optical defect inspection unit comprises:
    an optical inspection processor connected to the image sensor for calculating curvatures of an edge of the wafer in the images.

3. The dual-function wafer handling apparatus of claim 1, wherein the aligner comprises:
    a rotatable disk for placing the wafer thereon; and
    a motor configured to drive the rotatable disk.

4. The dual-function wafer handling apparatus of claim 3, wherein the rotatable disk is arranged between the optical defect inspection unit and the ID reader.

5. The dual-function wafer handling apparatus of claim 1, wherein the optical defect inspection unit is an automated optical defect inspection unit.

6. The dual-function wafer handling apparatus of claim 1, further comprising a controller configured to control a rotating speed of the aligner.

7. The dual-function wafer handling apparatus of claim 6, further comprising a warning device electrically connected to the controller, wherein the warning device is triggered when the controller receives an analysis result of abnormal from the optical defect inspection unit.

8. The dual-function wafer handling apparatus of claim 7, wherein the warning device is a sound alarm or an optical alarm.

9. The dual-function wafer handling apparatus of claim 1, further comprising a light source configured to provide lights to the wafer.

10. The dual-function wafer handling apparatus of claim 9, wherein the light source is a co-axial light source.

11. A dual-function wafer handling apparatus for handling a wafer, the apparatus comprising:
    an aligner for rotating the wafer;
    an ID reader for reading an ID of the wafer;
    an image sensor for capturing an image of an edge of the wafer;
    an optical inspection processor for capturing a profile of the edge of the wafer and calculating a curvature of the profile for analysis; and
    a frame for arranging the ID reader and the image sensor corresponding to the edge of the wafer, wherein the frame comprises:
        a rod;
        a first holder fastened on the rod and disposed corresponding to the edge of the wafer, wherein the ID reader is disposed on the first holder; and
        a second holder fastened on the rod and disposed corresponding to the edge of the wafer, wherein the image sensor is disposed on the second holder.

12. The dual-function wafer handling apparatus of claim 11, wherein the frame comprises a platform, and the aligner is placed on the platform.

13. The dual-function wafer handling apparatus of claim 12, wherein the first holder is arranged between the second holder and the platform.

14. The dual-function wafer handling apparatus of claim 11, wherein the frame further comprises a plurality of retaining nuts for fastening the first holder and the second holder on the rod.

15. The dual-function wafer handling apparatus of claim 14, wherein the frame further comprises a plurality of washers disposed between the retaining nuts and the first holder or second holder.

16. The dual-function wafer handling apparatus of claim 11, wherein the first holder comprises a plate portion and a flange portion, and a length of the first holder is adjustable by changing a screwing position between the plate portion and the flange portion.

17. The dual-function wafer handling apparatus of claim 11, wherein the second holder comprises a plate portion and a flange portion, and a length of the second holder is adjustable by changing a screwing position between the plate portion and the flange portion.

18. The dual-function wafer handling apparatus of claim 11, further comprising a light source disposed on the second holder.

19. A wafer handling apparatus, comprising:
a platform;
an aligner disposed on the platform and configured to rotate a wafer;
an optical defect inspection unit configured to capture an image of the wafer;
an ID reader configured to read an ID of the wafer;
a rod;
a first holder connected to the rod and disposed in between the optical defect inspection unit and the platform; and
a second holder connected to the rod and holding the ID reader.

20. The wafer handling apparatus of claim 19, wherein the second holder is disposed between the platform and the first holder.

* * * * *